United States Patent [19]

Noormohammadi et al.

[11] Patent Number: 5,011,662
[45] Date of Patent: Apr. 30, 1991

[54] DISSOLUTION TESTING MACHINE

[76] Inventors: Akbar Noormohammadi, 153 Earlifield Road, London SW18; Robert E. Dodd, 40 Fir Tree Ave., Wallingford Oxon OX10 OPD, both of England; Arnold H. Beckett, 16 Crestbrook Ave., Palmers Green, London 13, United Kingdom; Grahame K. J. Geeves, The Cobbles St. Marys Rd., Ascot, Berks, England

[21] Appl. No.: 70,145

[22] Filed: Jul. 2, 1987

Related U.S. Application Data

[63] Continuation of Ser. No. 585,394, Mar. 2, 1984, abandoned.

[30] Foreign Application Priority Data

Mar. 4, 1983 [GB] United Kingdom ............... 83 06055

[51] Int. Cl.$^5$ ............................................. G01N 31/00
[52] U.S. Cl. .................................... 422/68.1; 73/432.1; 134/135; 134/137; 134/157; 366/240; 366/256; 366/332; 422/64; 422/65
[58] Field of Search ............. 73/432 R, 432 Z; 436/2, 436/34; 422/64, 65, 68; 134/135, 137, 157; 99/323; 366/332, 256, 240

[56] References Cited

U.S. PATENT DOCUMENTS

| | | | |
|---|---|---|---|
| 970,872 | 9/1910 | Babcock | 134/137 |
| 2,646,807 | 7/1953 | Martin | 134/157 X |
| 3,572,648 | 3/1971 | Hanson | 366/349 |
| 3,654,852 | 4/1972 | Rosan, Sr. | 99/323 |
| 3,787,185 | 1/1974 | Rohrbaugh et al. | 422/64 |
| 3,791,221 | 2/1974 | Kirschner et al. | 73/432 Z |
| 3,801,280 | 4/1974 | Shah et al. | 436/2 |
| 3,802,272 | 4/1974 | Bischoff et al. | 73/432 Z |
| 3,951,605 | 4/1976 | Natelson | 422/65 |
| 4,108,602 | 8/1978 | Hanson et al. | 73/432 Z |
| 4,279,860 | 7/1981 | Smolen | 73/432 Z X |
| 4,363,782 | 12/1982 | Yamashita | 422/65 |

FOREIGN PATENT DOCUMENTS

| | | | |
|---|---|---|---|
| 0069986 | 1/1983 | European Pat. Off. | 422/65 |
| 2409222 | 4/1975 | Fed. Rep. of Germany . | |
| 2530065 | 3/1977 | Fed. Rep. of Germany | 73/432 Z |
| 0158277 | 1/1983 | Fed. Rep. of Germany | 73/432 Z |
| 1401663 | 7/1975 | United Kingdom | 73/432 Z |

Primary Examiner—Robert J. Hill
Attorney, Agent, or Firm—Oliff & Berridge

[57] ABSTRACT

A dissolution testing machine has a container for a liquid and a holder for pellets, a support for supporting the holder within the container and a drive enabling the holder to be reciprocated via its support so that solvent flushes into and out of the holder.

The holder may be a mesh tube, or a solid walled tube, closed at both ends by an apertured member. A set of containers may receive the holder successively, each container containing a solvent of the same or different characteristics.

9 Claims, 3 Drawing Sheets

DISSOLUTION TESTING MACHINE

This is a continuation of application Ser. No. 585,394 filed Mar. 2, 1984 now abandoned.

BACKGROUND OF THE INVENTION

This invention relates to dissolution testing machines capable of measuring the dissolution rate of chemicals from tablets or pellets. Such machines are, in particular, used in the pharmaceutical industry in connection with measuring the controlled rate of release of drugs.

In the past, two main standard methods have been used to conduct experiments on the rate of release of chemicals. In the first, the tablets, capsules, pellets or the like (hereinafter called 'pellets'), are placed in the bottom of a standard container, and a paddle of standard shape is rotated about a vertical axis in a standard position in the container. However, the tendency is for the pellets to form a heap in the bottom of the container directly below the paddle, and the solution formed tends to maintain a gradient with the highest concentration at the bottom and the lowest at the top. Although standardized, as between tests, such an apparatus does not provide a true indication of rate of dissolution of the pellets when taken internally by a patient.

In the second method, the pellets are placed inside a perforated basket of generally cylindrical shape, which basket is itself rotated about its central longitudinal axis in the liquid. However, the tendency then is to form a film of chemical in solution around the pellets, with a higher concentration of solution within the basket than outside it. An increase in the speed of rotation may increase the dissolution rate, but may also cause abrasion of the pellets by the basket mesh, which thus falsifies the results in an opposite direction.

A third unofficial method employs a rotating bottle, in effect mounted on an arm of a rotating wheel in a vertical plane, so that the bottle is tipped upside down once in every revolution. However, since the bottle must be liquid tight during this operation, it becomes very difficult to extract samples for testing at different time intervals, and the process is inconvenient and labor intensive.

SUMMARY OF THE INVENTION

The invention aims to provide a machine which allows reproducible testing of the dissolution rate of pellets, permits sampling either manually or automatically, and which does not suffer from the "retarding" effects common in known machines due to concentration gradients in the solvent due to inefficient flushing of the solvent over the pellets.

Accordingly, the invention proposes a dissolution testing machine comprising a container for a liquid and a holder for pellets, means supporting the holder within the container, and drive means enabling the holder to be reciprocated via its support means so that solvent flushes into and out of the holder.

Such a machine preferably employs an elongated cylindrical container, similar to a test tube, and a cylindrical holder coaxial within the container and reciprocated along that axis. The holder may be a mesh basket, or a solid tube closed at its ends with mesh.

The invention also proposes a method of testing the dissolution of chemicals, wherein the chemicals are placed in a holder which is open at least at top and bottom and said holder is reciprocated up and down in a container of solvent in standard conditions.

In a preferred method, said holder is moved successively from one to another of a plurality of containers, each container holding a solvent of the same or different characteristics.

BRIEF DESCRIPTION OF THE DRAWINGS

In order that the invention shall be clearly understood, an exemplary embodiment of a machine will now be described with reference to the accompanying drawings, in which.

DESCRIPTION OF THE PREFERRED EMBODIMENT

Figure 1:
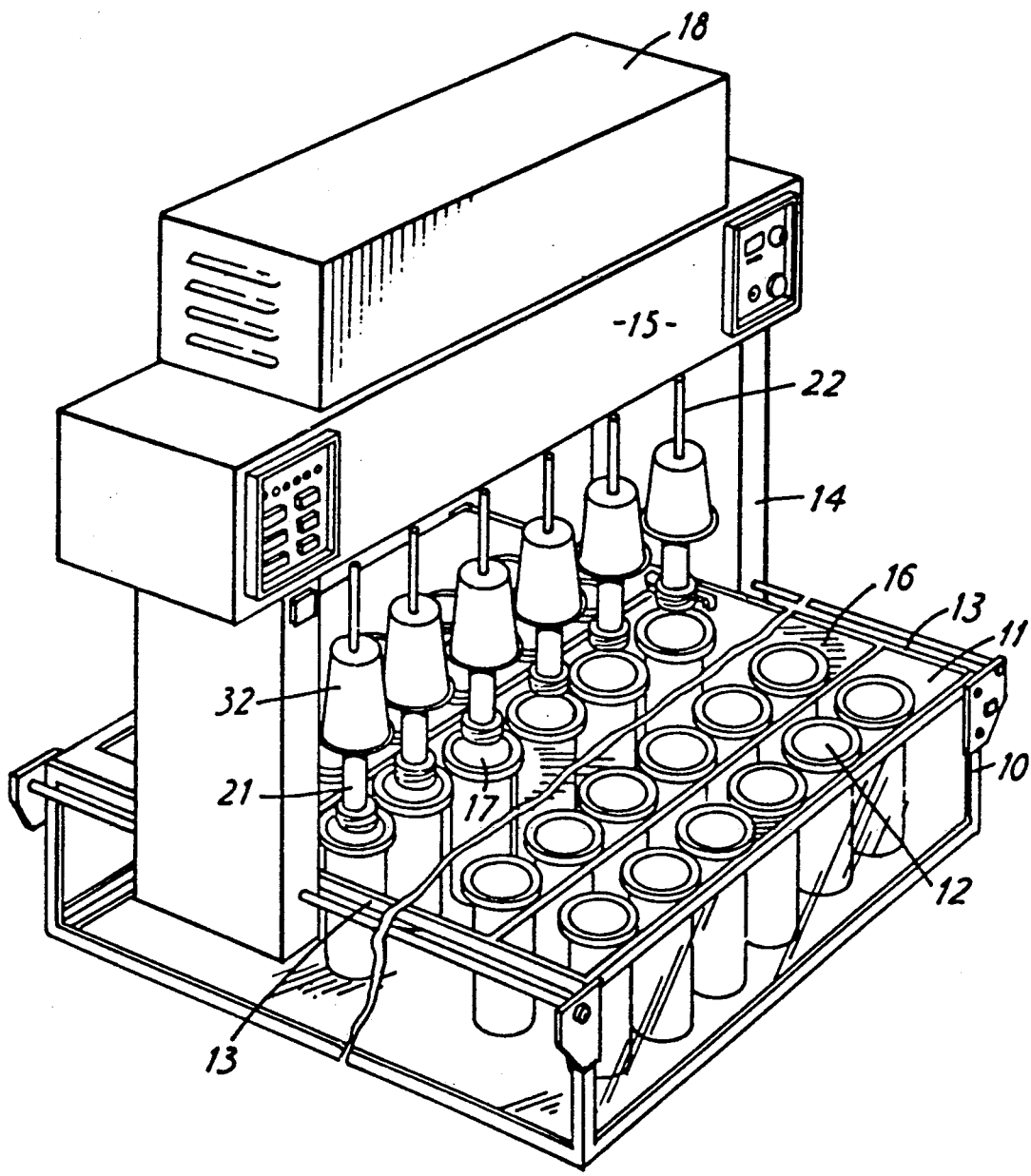
FIG. 1 shows an overall schematic view of the machine according to the invention.

In FIG. 1, a frame 10 supports a temperature controlled bath (not shown) which almost completely fills it. The top of the frame is covered by a matrix or framework 11 which defines a plurality of positions arranged in rows 16 and columns 17, each position 12 being designed to receive a glass container which is approximately the shape and size of a large test tube. The bath is maintained at a constant temperature of approximately 37 degrees, thus maintaining the contents of the tubes at that temperature. A bridge structure 14 straddles the frame 10 and is movable by sliding along guide members on two upper sides 13 of the frame. Thus, the bridge 14 can be brought successively to positions above each of the rows of containers. The bridge 14 supports six mesh baskets 21 which are suspended below it, and also drive means 15 for controlling movement of the baskets. A control unit 18 controls the operation of the machine.

Figure 2:
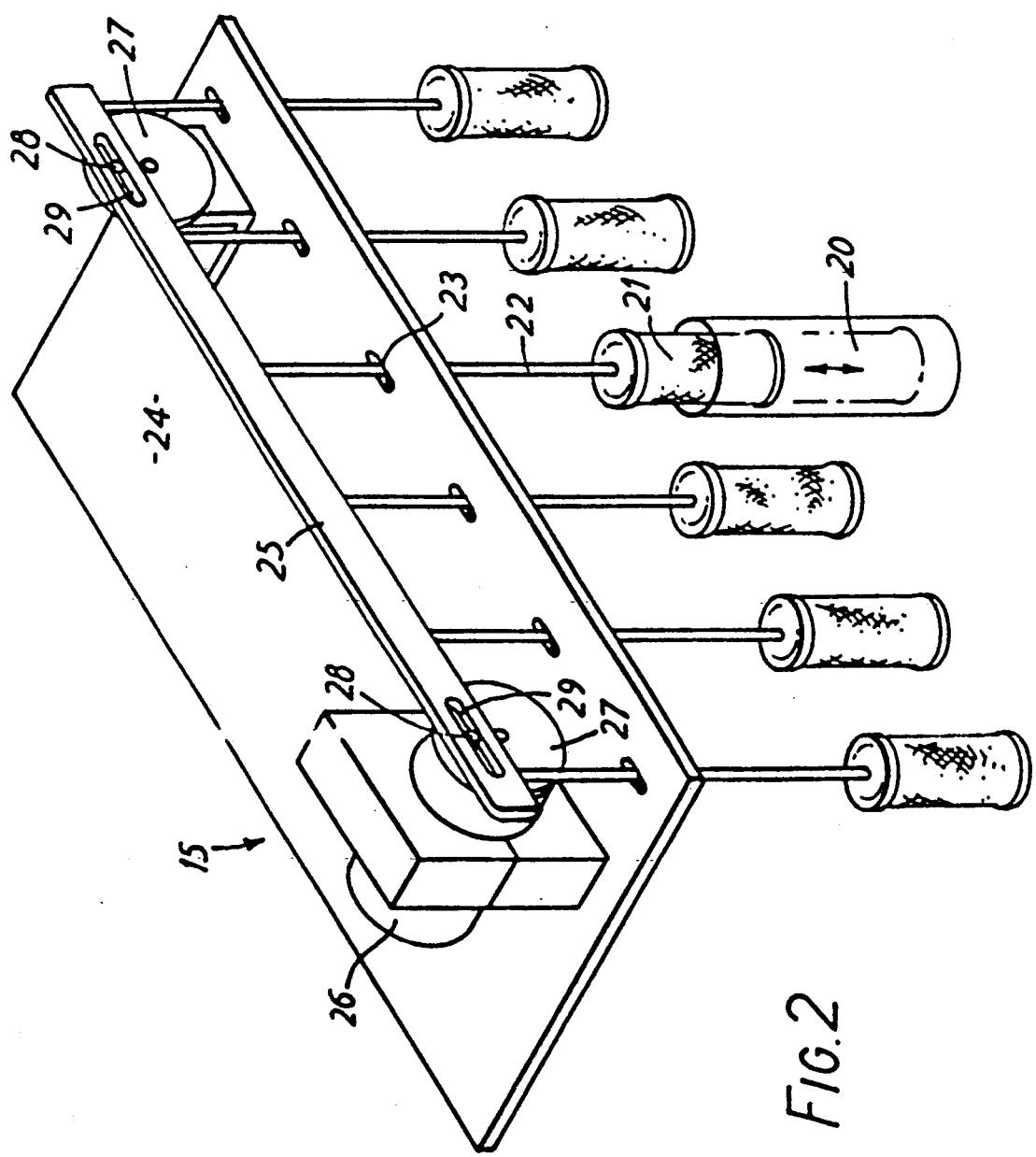
FIG. 2 shows the support means and drive means.

FIG. 2 shows an enlarged and a more detailed view of the drive means and baskets supported on the bridge 14. A set of six glass containers 20 supported in the heated bath are arranged in the first row (only one container is shown). Directly above each container is suspended a small mesh basket 21 which is approximately 10 centimeters long and 2.5 cm in diameter. Each basket 21 is supported on a rod 22 which extends through a hole 23 in a support plate 24, and is fixed on a transverse bar 25. A motor 26 drives synchronously two discs 27 at a speed of between 5 and 50 r.p.m, preferably about 20 r.p.m. A pin 28 on each disc engages slots 29 in the beam 25 so that rotation of the discs 27 causes the whole structure supporting the series of baskets 21 to move gently up and down.

Figure 3:
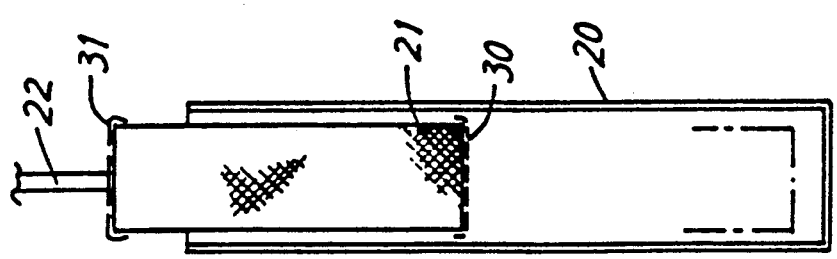
FIG. 3 shows a container and a mesh basket holder for the machine.

The nature of the container and basket can be seen from FIG. 3. The container 20 is made of glass and has the shape of a right cylinder with an open top. The mesh basket 21 is made preferably of metal and is open at both top and bottom. The mesh may have any desired hole size. The bottom of the mesh basket is closed by a layer of soft and/or resilient gauze fabric 30 held by a small elastic band. The use of gauze prevents the pellets from being abraded when contacting the same. At the top, the basket is closed by a perforated plastic cap 31 which clips onto a bead on the top edge of the basket. The rod 22 is fixed directly to the cap 31. A splash cover 32 (FIG. 1) may be provided. The materials used must be inert to both the solvent and the chemicals of the pellet, and must not absorb these substances.

In use, pellets to be dissolved are placed in the baskets, and the containers 20 are filled approximately three-quarters with a solvent, sufficient so that the pellets are not raised right out of the solvent. The up and down movement causes the solvent to be flushed in and out of the baskets in a controlled fashion, so as to produce dissolution of the pellets. The pellets are levitated with each downward stroke.

In an alternative embodiment, the holder may be a solid glass tube which will abrade the pellets and is open at both the top and bottom. The openings are then covered by soft and/or resilient mesh discs or fabric and held in position by a perforated plastic cap. Any suitable construction can be used which allows easy insertion of pellets, and easy liquid flow. The perforations of the cap and the mesh size of the disc or fabric may be chosen according to need. For example, very fine holes may be required to retard tablets which disintegrate before they dissolve.

Since the controlled experiments normally to be carried out with the machine requires a series of tests of varying duration and with solvents of varying characteristics or concentrations, the machine is arranged so that the bridge 14, after performing one set of tests on the pellets in the first row of containers, is moved along the framework 10 until the baskets are aligned above the second row of containers. These containers may contain the same solvents at a different concentration, or a different solvent, and a further test can be performed for the same or a different time period. The dissolution rate in the first row of containers can be determined from the solution strength remaining in those containers. Thus, the machine shown has the capacity to perform six tests simultaneously, using the same or different pellets in different containers, and to repeat this operation six times in different solvents, or for different periods. Between each test, the baskets are raised to their highest position and the bridge 14 indexed sideways.

In a typical test, a single solvent is used in all cases, but with a different pH value in each row. The six successive tests would then be as follows:

| Row | 1 | 2 | 3 | 4 | 5 | 6 |
| --- | --- | --- | --- | --- | --- | --- |
| pH | 1.5 | 4.5 | 6.9 | 6.9 | 7.2 | 7.5 |
| Time | 1 hr | 1 hr | 2 hrs | 2 hrs | 2 hrs | 4 hrs |

Such a test would approximate the effect of gastric juices acting on a capsule swallowed by a person, and would be of use in determining the likely effects of swallowing a capsule containing a multitude of pellets of different solubilities intended to provide drug release throughout a period of 12 hours.

The measurement of the solution strengths left in each of the six containers forming one column and representing one set of test results can be performed in a number of ways. They can be tested manually as the sequence proceeds. Or the drive means and baskets can be replaced by a separate 'head' consisting of a set of six dip tubes which can sample and test all six containers of one row. By indexing the head sideways using the bridge 14, the dip tubes can be lowered into successive rows of containers and a set of readings produced for each column by each dip tube. Such a successive sampling can be carried out after completion of the actual dissolution tests.

Alternatively, the dip tubes could be mounted on the same head as the baskets, and arranged to sample the solutions one row behind the row currently receiving the pellets. In this case, the bridge 14 would need to index one step more than the numbers of rows of containers.

The control unit 18 may be manually controlled or micro-processor operated, so that all the indexing and timing can be pre-determined by hard or soft programming. This can also be applied to the subsequent sampling.

Figure 4:
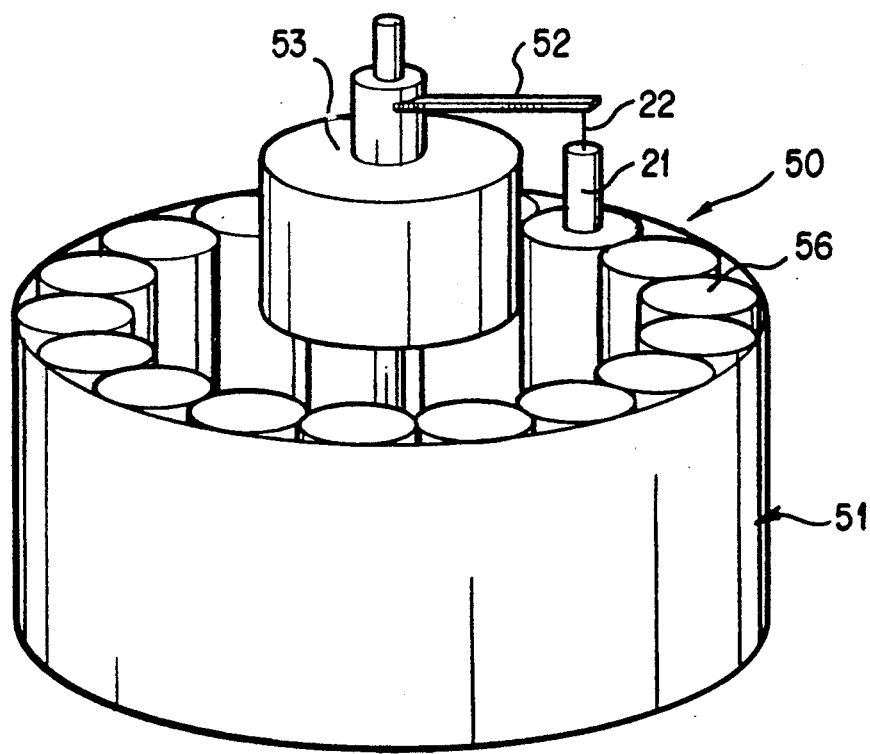
FIG. 4 shows a circular array of containers arranged in a cylindrical tank.

The invention can be applied to less complex machines than this, which is designed for batch sampling. A machine having one basket mounted on a head which is rotatable in the middle of a circular array of containers is also envisaged. Control may again be manual or automatic. FIG. 4 illustrates a circular array of containers 50 (comprised of individual containers 56) arranged in a cylindrical tank 51. A holder 21 is supported by a rod 22 affixed to a support arm 52. The support arm 52 is secured to a housing 53 capable of circular rotation and up and down reciprocation, by means known to those skilled in the art. During operation, the holder 21 and its respective contents are reciprocated up and down in a container 56 for a determined time, removed and rotated to the next successive container 56 and, again, reciprocated up and down, etc. until the entire dissolution test is complete.

It will be understood that the above description of the present invention is susceptible to various modifications, changes and adaptations.

What is claimed is:

1. In a dissolution testing machine consisting essentially of a container for a liquid, a fluid passable holder for a sample, support means for supporting said holder within said container, and drive means for said holder and said support means;

the improvement wherein the fluid passable holder comprises resilient gauze fabric at a bottom portion thereof to prevent abrasion of a sample when it is contacted therewith, and wherein the drive means is for moving said support means in such a manner that said holder is vertically reciprocated within said container without rotation about an axis so that liquid in said container flushes into and out of the holder, thereby causing a sample in the holder to move up and down in response to liquid flushing into and out of said holder.

2. The machine as defined in claim 1, wherein said container is tubular.

3. The machine as defined in claim 1, wherein said holder is a solid walled tube having resilient gauze fabric closing the holder at its top and bottom.

4. The machine as defined in claim 1, wherein said holder is a mesh-walled tube having resilient gauze fabric closing the holder at its top and bottom.

5. The machine as defined in claim 1, which includes a set of said containers, wherein said support means and said drive means can be moved so that the holder is supported and vertically reciprocated successively in each container of the set.

6. The machine as defined in claim 5, wherein the containers of said set of containers are arranged in a row and said support means and said drive means can be moved linearly so that the holder is supported and vertically reciprocated successively in each container of the set.

7. The machine as defined in claim 6, which includes a plurality of said sets of container and a corresponding plurality of said holders so that a plurality of dissolution tests can be carried out simultaneously.

8. The machine as defined in claim 5, wherein said support means includes a movable frame.

9. The machine as defined in claim 8, wherein the movable frame can be moved through a number of positions equal to one more than the number of containers in the set of containers.

* * * * *